United States Patent
Simesen et al.

(10) Patent No.: US 6,933,136 B2
(45) Date of Patent: Aug. 23, 2005

(54) METHOD FOR MAKING RECOMBINANT PROTEINS

(75) Inventors: Ruth Buemann Simesen, Vanlose (DK); Anette Amstrup Pedersen, Soborg (DK); Steffen Faisst, Farum (DK); Jan Eric Jensen, København S (DK); Dietmar Weilguny, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/664,775

(22) Filed: Sep. 17, 2003

(65) Prior Publication Data

US 2004/0115776 A1 Jun. 17, 2004

Related U.S. Application Data

(60) Provisional application No. 60/416,566, filed on Oct. 7, 2002.

(30) Foreign Application Priority Data

Sep. 20, 2002 (DK) .................................. PA 2002 01384

(51) Int. Cl.⁷ ................................................ C12P 21/00
(52) U.S. Cl. .................... 435/69.6; 435/320.1; 435/325; 530/381
(58) Field of Search ............................ 435/69.1, 69.6, 435/320.1, 325; 530/381

(56) References Cited

U.S. PATENT DOCUMENTS

| | | | | |
|---|---|---|---|---|
| 4,784,950 A | * | 11/1988 | Hagen et al. | 435/69.6 |
| 5,888,774 A | * | 3/1999 | Delcuve | 435/69.6 |
| 5,985,607 A | | 11/1999 | Delcuve et al. | 435/69.1 |
| 6,455,275 B1 | | 9/2002 | Axel et al. | 435/69.1 |

FOREIGN PATENT DOCUMENTS

| | | |
|---|---|---|
| EP | 0 999 280 A3 | 10/1999 |
| EP | 0 999 280 A2 | 10/1999 |
| WO | WO 96/19573 | 6/1996 |
| WO | WO 97/04122 A1 | 2/1997 |
| WO | WO 97/46687 A1 | 12/1997 |
| WO | WO 99/07866 A1 | 2/1999 |
| WO | WO 01/83725 A1 | 11/2001 |
| WO | WO 02/14525 A2 | 2/2002 |
| WO | WO 02/48379 A1 | 6/2002 |

OTHER PUBLICATIONS

Poljak et al. Nucleic Acid Research 22(21): 4386–4394 (1994).*
Blasquez et al. Journal of Biological Chemistry 264(35): 21183–21189 (1989).*
Ostermeier et al. Nucleic Acid Research 31(12): 3257–3266 (2003).*
Phi–Van et al., Molecular and Cellular Biology, vol. 10, No. 5, pp. 2302–2307 (1990).
Klehr et al., Biochemistry, vol. 30, pp. 1264–1270 (1991).
Singh et al., Nucleic Acids Research, vol. 25, No. 7, pp. 1419–1425, (1997).
International Search Report mailed Apr. 2, 2004.

* cited by examiner

*Primary Examiner*—Karen Cochrane Carlson
*Assistant Examiner*—Anand Desai
(74) *Attorney, Agent, or Firm*—Len S. Smith; Reza Green; Richard Bork

(57) ABSTRACT

The invention provides nucleic acid molecules and vector constructs comprising scaffold/matrix attachment regions and methods of using such scaffold/matrix attachment regions for the industrial production of recombinant proteins and polypeptides.

38 Claims, 10 Drawing Sheets

METHOD FOR MAKING RECOMBINANT PROTEINS

CROSS REFERENCE TO RELATED PATENT APPLICATIONS

This application claims priority under 35 U.S.C. 119 from Danish Patent Application No. PA 2002 01384, filed Sep. 20, 2002, and the benefit of U.S. Provisional Patent Application No. 60/416,566, filed Oct. 7, 2002, the contents of which are fully incorporated herein by reference.

FIELD OF THE INVENTION

The present invention relates to scaffold/matrix attachment regions and their use for the production of recombinant proteins.

BACKGROUND OF THE INVENTION

Advances in cell culture and recombinant DNA technologies have facilitated the expression of a variety of proteins of therapeutic or other economic value using genetically engineered cells. The expression of many biologically active therapeutic proteins, which are derived from higher eukaryotic sources, often requires specific post-translational modifications which do not naturally occur in lower eukaryotic or prokaryotic cells, thus necessitating the use of cells derived from higher eukaryotic sources. For example, the expression of glycoproteins in mammalian cells has the advantage of providing proteins which contain natural glycosylation. Mammalian-produced glycoproteins contain outer chain carbohydrate moieties, which are markedly different from the outer chain carbohydrate moieties present on glycoproteins produced from lower eukaryotes. The use of mammalian cells as hosts for the production of secreted mammalian proteins has the significant advantage over secretion from lower eukaryotes in that mammalian cells have a secretory system that readily recognizes and properly processes secretion-directed proteins, which is not necessarily true for lower eukaryotes.

Scaffold Attachment Regions (SAR), also called Matrix Attachment Regions (MAR) or Scaffold/Matrix Attachment Regions (S/MAR) are non-consensus-like AT-rich DNA elements several hundred base pairs (bp) in length, which organize the nuclear DNA of the eukaryotic genome into some 60,000 chromatin domains, 4–200 kbp loops, by periodic attachment to the protein scaffold or matrix of the cell nucleus. S/MARs have been isolated from regions surrounding actively transcribed genes but also from introns, centromeres and teleomeric regions and have been found to collaborate with enhancers to help regulate transcription by controlling the chromatin state of DNA. The observations that S/MARs positively interact with enhancers, form loop domains and often are located at the borders of transcriptionally active domains have led to the idea of using S/MARs as flanking elements around transgenes, forming so called mini-domains, in order to protect transgenes or expression cassettes from transcriptional silencing and the effects of surrounding heterochromatin (transcriptionally inactive chromatin) as well as possibly increase gene expression. Several publications have shown that S/MARs in a flanking position can strongly stimulate expression of transgenes, as well as reduce expression variability between cell clones (position effects). Moreover, due to the character of a mini-domain, expression should be independent from the integration site.

U.S. Pat. No. 5,985,607 discloses the use of certain SAR elements for expression of EPO and tPA. In Biochemistry, 30:1264–1270, 1991, the effect of other SAR elements on expression of the human interferon β is disclosed. Phi-Van et al. in Mol. Cell. Biol, 10:2302–2307, 1990 ("The chicken lysozyme 5' matrix attachment region increases transcription from a heterologous promoter in heterologous cells and dampens position effects on the expression of transfected genes") discloses the influence on gene expression of a MAR element located upstream of the chicken lysozyme gene. WO/9704122 discloses a method for producing polypeptides in plants with possible use of nuclear scaffold attachment region sequences and WO 02/14525 discloses an animal expression vector comprising β-globulin MAR or SAR sequences.

The proteins involved in the clotting cascade, including, e.g., Factor VII, Factor VIII, Factor IX, Factor X, and Protein C, are proving to be useful therapeutic agents to treat a variety of pathological conditions. Because of the many disadvantages of using human plasma as a source of pharmaceutical products, it is preferred to produce these proteins in recombinant systems. The clotting proteins, however, are subject to a variety of co- and post-translational modifications, including, e.g., asparagine-linked (N-linked) glycosylation; O-linked glycosylation; and γ-carboxylation of Glu residues. For this reason, it is preferable to produce them in mammalian cells, which are able to modify the recombinant proteins appropriately. Production of recombinant proteins within mammalian cells can be difficult because of a low genetic stability of the recombinant gene and/or silencing of the recombinant gene. Several molecular mechanisms have been reported that may lead to gene silencing, e.g., DNA methylation and histone deacetylation.

Thus, there is a need in the art to overcome the deficiencies of the known methods for making clotting proteins by providing mammalian production strains with a higher genetic stability in large-scale production to produce industrial quantities of the clotting proteins, particularly recombinant human Factor VII or Factor VII-related polypeptides.

SUMMARY OF THE INVENTION

The present invention is based on the discovery of new S/MAR elements from hamster-derived CHO and BHK cells, which may be used for increasing and stabilizing the expression yield of recombinant proteins in mammalian cells. The S/MAR elements are thought to increase the genetic stability of nearby transcription cassettes and to inhibit gene silencing by interfering with mechanisms such as DNA methylation and histone deacetylation. Furthermore, the presence of S/MAR elements is thought to decrease clone-to-clone variability through decreasing position effects, thereby minimizing the need of screening work to identify high-yielding producer cell clones.

The S/MAR elements will typically be inserted upstream and downstream to the DNA encoding the desired protein and will be introduced in the host mammalian cell line on expression vectors comprising the necessary elements for expression of heterologous proteins in transfected cells.

Thus, in one embodiment, the invention relates to a method for production of Factor VII polypeptides or Factor VII-related polypeptides comprising a) transfecting a mammalian cell with an expression vector comprising a nucleic acid molecule encoding Factor VII or a Factor VII-related polypeptide, expression control regions operatively linked to thereto and at least one S/MAR element; b) culturing the transfected cell under conditions for expression of Factor VII or a Factor VII-related polypeptide and c) isolating the expressed polypeptide by suitable means.

In one embodiment, the vector comprises two S/MAR elements flanking the DNA encoding Factor VII or a Factor VII-related polypeptide and the expression control regions. The S/MAR elements may be selected from the group consisting of SEQ ID NO:1 and SEQ ID NO:2, functional fragments thereof, and sequences that are at least about 70% homologous thereto as determined by pair wise DNA sequence alignment using matching methods like the BLAST (Basic Local Alignment Search Tool) algorithm (Altschul, S. F. et al., 1990, "Basic local alignment search tool". J. Mol. Biol. 215:403–410; and Altschul, S. F. et al., 1997, "Gapped BLAST and PSI-BLAST: a new generation of protein database search programs". Nucl. Acids Res. 25:3389–3402).

In a further embodiment, the S/MAR elements will be at least about 75%, at least about 80%, at least about 85%, at least about 90%, or about 95% or more homologous to SEQ ID NO:1 or SEQ ID NO:2, respectively, as determined by pair wise DNA sequence alignment using matching methods like the BLAST algorithm. Examples of S/MAR sequences homologous to SEQ ID NO:1 and SEQ ID NO:2 include SEQ ID NOS:3–5.

The S/MAR elements may be the same or different and may be located in a distance of from 0 to 10 kb from the DNA encoding Factor VII or a Factor VII-related polypeptide and the expression control regions.

In one embodiment the vector expressing Factor VII or a FVII-related polypeptide will comprise two identical S/MAR elements. In a further embodiment, such S/MAR elements are selected from the group consisting of SEQ ID NOS:1–5.

In a still further embodiment, the vector expressing FVII or a FVII-related polypeptide comprises two S/MAR elements which are different from each other with respect to base pairs and numbers. Such S/MAR elements will preferably be selected from the group consisting of SEQ ID NOS:1–5. The vector can comprise any combination of sequences selected from SEQ ID NOS:1–5.

In another embodiment, the present invention is related to a method for production of polypeptides or proteins in transfected mammalian cells comprising a) transfecting a mammalian cell with an expression vector comprising a nucleic acid molecule encoding a polypeptide or protein, expression control regions operatively linked thereto and at least one S/MAR element selected from the group consisting of SEQ ID NO:1 and SEQ ID NO:2, functional fragments thereof, and sequences that are at least 70% homologous thereto; b) culturing the transfected cell under conditions for expression of the desired polypeptides or protein and c) isolating the expressed product by suitable means.

The S/MAR elements will in be at least about 75%, at least about 80%, at least about 85%, at least about 90%, or at least about 95% homologous to SEQ ID NO:1 or SEQ ID NO:2, respectively, as determined by pair wise DNA sequence alignment using matching methods like the BLAST algorithm. Examples of S/MAR sequences homologous to SEQ ID NO:1 and SEQ ID NO:2 include SEQ ID NOS:3–5.

The S/MAR elements may be the same or different and may be located in a distance of from 0 to about 10 kb from the DNA encoding the desired polypeptide and the expression control regions.

In one embodiment of the present invention, the vector comprises two S/MAR elements being the same and selected from the group consisting of SEQ ID NOS:1–5.

In a further embodiment, the vector comprises two S/MAR elements which are different from each other with respect to base pairs and numbers. In this embodiment, the pair of S/MAR elements can be any combination of SEQ ID NOS:1–5.

In a further embodiment, the present invention is related to an isolated DNA molecule having a nucleotide sequence selected from the group consisting of SEQ ID NO:1 and SEQ ID NO:2 and sequences that are at least 70% homologous thereto. The invention also provides isolated DNA molecules comprising a sequences that hybridizes to such an isolated DNA molecule under stringent conditions.

In a still further embodiment, the invention is related to mammalian cell lines transfected with an expression vector comprising a nucleic acid molecule encoding Factor VII or a Factor VII-related polypeptide, expression control regions operatively linked to thereto and at least one S/MAR element.

In still a further embodiment, the invention is related to mammalian cell lines transfected with an expression vector comprising a nucleic acid molecule encoding a polypeptide or protein, expression control regions operatively linked thereto, and at least one S/MAR element selected from (a) the group consisting of SEQ ID NO:1 and SEQ ID NO:2, (b) functional fragments thereof, and (c) sequences being at least 70% homologous thereto

BRIEF DESCRIPTION OF THE DRAWINGS

The invention is further explained with reference to the drawings in which.

DETAILED DESCRIPTION OF THE INVENTION

Definitions

Figure 1:
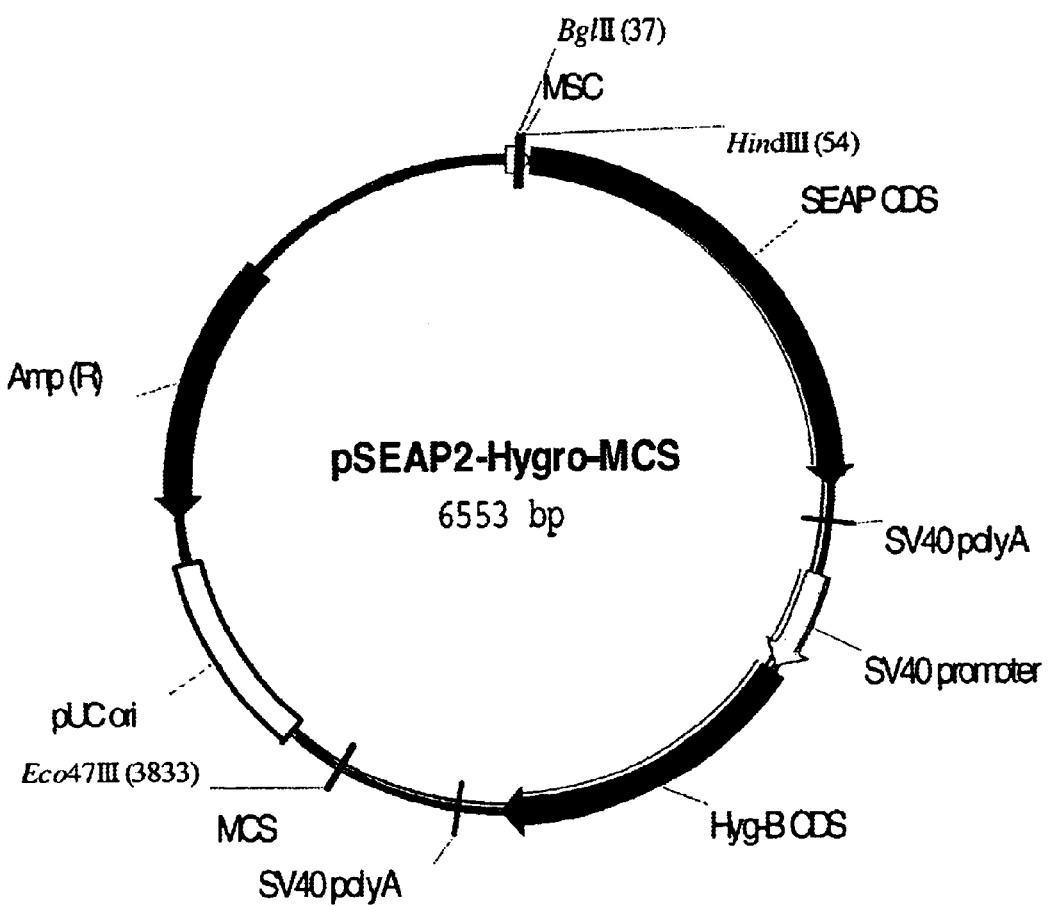
FIG. 1 shows plasmid pSEAP2-Hygro-MCS.

The terms Scaffold Attachment Regions (SAR) or Matrix Attachment Regions (MAR) or Scaffold/Matrix Attachment Regions (S/MAR), as used herein, refer to non-consensus-like AT-rich DNA elements several hundred base pairs (bp) in length, which organize the nuclear DNA of the eukaryotic genome into some 60,000 chromatin domains, 4–200 kbp loops, by periodic attachment to the protein scaffold or matrix of the cell nucleus. S/MAR elements are typically found in non coding regions such as flanking regions, such as regions upstream or downstream to a coding region, and introns.

The S/MAR elements according to the present inventions were isolated from BHK cells and CHO cells, e.g. CHO cell line DG44 (Urlaub, G. et al., 1983, "Deletion of the diploid dihydrofolate reductase locus from cultured mammalian cells". Cell 33:405–412).

Methods for identifying S/MAR elements include computer prediction techniques, such as using MAR-FINDER software, that allow one to search for several relevant sequence motifs, such as origin of replication motifs, AT-rich sequences, TG-rich sequences, and curved DNA sequences, (Singh, G. B., Kramer, J. A. and Krawetz, S. A. (1997). "Mathematical model to predict regions of chromatin attachment to the nuclear matrix". Nucl. Acids Res. 25:1419–1425).

A DNA sequence "with at least 70% homology" to another sequence refers to a sequence determined to be at least 70% homologous to the other sequence as measured by pairwise DNA sequence alignment using matching methods like the BLAST algorithm.

The term "functional fragments" of SEQ ID NO:1 and SEQ ID NO:2 as used herein means fragments of said sequences of a size large enough to have the desired effect on expression yields. Such functional fragments typically contain at least about 300 bp of SEQ ID NO:1 or SEQ ID NO:2. The fragments will preferably be a consecutive sequence of the original sequence. Examples of such fragments include SEQ ID NO:3 (from bp 543 to bp 2545 of SEQ ID NO:1); SEQ ID NO:4 (from bp 437 to bp 2715 of SEQ ID NO:1); and SEQ ID NO:5 (having a 12 base pair deletion in the GT rich region of SEQ ID NO:1 located at bp 1551 to 1604).

The term flanking means that the sequences in question are either directly connected to the expression cassette or are connected by linking DNA sequences which may be up to about 10 kb or more in length, as long as such linking sequences do not interfere with the desired effect of the S/MAR elements. The expression cassette comprises, at a minimum, a gene of interest and expression control elements operatively linked thereto. Typically, S/MAR elements flank both sides, 5'-upstream and 3'-downstream, of the expression cassette. The orientation of the S/MAR elements is optional. The expression cassette can be flanked by all possible combinations of the S/MAR sequences selected from group consisting of SEQ ID NOS:1–5. The control elements usually comprise regulatory elements such as transcriptional promoters, enhancers, RNA polymerase binding sites, polyadenylation sites, translation initiation signals, and termination signals, suitable examples of which are known in the art.

The polypeptide or protein may be any polypeptide or protein, e.g. aprotinin, tissue factor pathway inhibitor or other protease inhibitors, insulin or insulin precursors, human or bovine growth hormone, interleukin, glucagon, GLP-1, GLP-2, IGF-I, IGF-II, tissue plasminogen activator, transforming growth factor α or β, platelet-derived growth factor, GRF (growth hormone releasing factor), immunoglobulins, EPO, TPA, protein C, blood coagulation factors such as FVII, FVIII, FIV and FXIII, exendin-3, exentidin-4, other enzymes, or functional analogues thereof. In the present context, the term "functional analogue" is meant to indicate a protein with a similar function as the native protein. The protein may be structurally similar to the native protein and may be derived from the native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence.

Human Factor VII polypeptide refers to a polypeptide having the amino acid sequence disclosed in U.S. Pat. No. 4,784,950 (wild-type Factor VII). As used herein, "Factor VII" or "Factor VII polypeptide" encompasses wild-type Factor VII, as well as variants of Factor VII that exhibit substantially the same or improved biological activity relative to wild-type Factor VII. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

As used herein, "Factor VII-related polypeptides" encompasses polypeptides, including variants, in which the Factor VIIa biological activity has been substantially modified or reduced relative to the activity of wild-type Factor VIIa. These polypeptides include, without limitation, Factor VII or Factor VIIa that has been chemically modified and Factor VII variants into which specific amino acid sequence alterations have been introduced that modify or disrupt the bioactivity of the polypeptide.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., *J. Biol. Chem.* 272:19919–19924, 1997); (ii) measuring Factor X hydrolysis in an aqueous system (see, Example 5 below); (iii) measuring its physical binding to TF using an instrument based on surface plasmon resonance (Persson, *FEBS Letts.* 413:359–363, 1997); (iv) measuring hydrolysis of a synthetic substrate; and (v) measuring generation of thrombin in a TF-independent in vitro system.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of wild-type Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids. Non-limiting examples of Factor VII variants having substantially the same biological activity as wild-type Factor VII include S52A-FVIIa, S60A-FVIIa (lino et al., *Arch. Biochem. Biophys.* 352: 182–192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., *Biotechnol. Bioeng.* 48:501–505, 1995); oxidized forms of Factor VIIa (Kornfelt et al., *Arch. Biochem. Biophys.* 363:43–54, 1999). FVII variants as disclosed in PCT/DK02/00189; FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); and FVII variants as disclosed in WO 01/58935 (Maxygen ApS).

Non-limiting examples of FVII variants having increased biological activity compared to wild-type FVIIa include. FVII variants as disclosed in WO 01/83725, WO 02/22776, Danish patent application PA 2001 01413, Danish patent application PA 2001 01627; and FVIIa variants with enhanced activity as disclosed in JP 2001061479 (Chemo-Sero-Therapeutic Res Inst.).

Non-limiting examples of Factor VII variants having substantially reduced or modified biological activity relative to wild-type Factor VII include R152E-FVIIa (Wildgoose et al., *Biochem* 29:3413–3420, 1990), S344A-FVIIa (Kazama et al., *J. Biol. Chem.* 270:66–72, 1995), FFR-FVIIa (Holst et al., *Eur. J. Vasc. Endovasc. Surg.* 15:515–520, 1998), and Factor VIIa lacking the Gla domain, (Nicolaisen et al., *FEBS Letts.* 317:245–249, 1993). Non-limiting examples of chemically modified Factor VII polypeptides and sequence variants are described, e.g., in U.S. Pat. No. 5,997,864.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extra chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The vector is preferably an expression vector in which the encoding DNA sequence is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

In case of FVII the vector system may comprise two separate vectors being capable of expressing FVII and an endoprotease, respectively. In this embodiment the mammalian cells are co-transfected with the two vectors and then cultured in a suitable culture medium. Alternatively an already established Factor VII expression clone may be transfected with a vector capable of expressing the endoprotease. The vector system may also comprise one single vector comprising the FVII expression cassette and the endoprotease expression cassette. An example of suitable endoproteases is the KEX2 enzyme.

The mammalian cells may include Chinese hamster ovary (CHO) cells, HeLa cells, baby hamster kidney (BHK) cells, COS cells, HEK 293 cells, or other immortalized cell lines available, e.g., from the American Type Culture Collection.

Examples of suitable mammalian cell lines include the COS (ATCC CRL 1650), BHK (ATCC CRL 1632, ATCC CCL 10), CHL (ATCC CCL39), HEK 293 (ATCC CRL 1573), and CHO (ATCC CCL 61) cell lines.

Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appl. Genet.* 1 (1982), 327–341; Loyter et al., *Proc. Natl. Acad. Sci. USA* 79 (1982), 422–426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841–845.

The promoter may be any DNA sequence which shows transcriptional activity in the host cell and may be derived from genes encoding proteins either homologous or heterologous to the host cell. Examples of suitable promoters for directing the transcription of the encoding DNA in mammalian cells include the SV40 promoter (Subramani, S. et al., 1981, "Expression of the mouse dihydrofolate reductase complementary deoxyribonucleic acid I simian virus 40 vector", *Mol. Cell. Biol.* 1:854–864), the MT-1 (metallothionein gene) promoter (Palmiter, R. D. et al., 1983, "Metallothionein-human HG fusion genes stimulate growth of mice". *Science* 222:809–14), and the human cytomegalovirus immediate-early promoter (Nelson, J. A and Groudine, M., 1986, "Transcriptional regulation of the human cytomegalovirus major immediate-early gene is associated with induction of DNase I hypersensitive sites". Mol. Cell. Biol 6:452–461).

The encoding DNA sequence may also, be operably connected to a suitable terminator, such as the human growth hormone terminator or the ADH3 terminator.

The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The vector will also preferably contain a signal peptide coding region, which codes for an amino acid sequence linked to the amino terminus of the FVII polypeptide which can direct the expressed FVII polypeptide into the cell's secretory pathway of the host cell. The signal may be homologous or heterologous to the host mammalian cell line and it may be the natural signal peptide.

Finally, the vector may comprise a DNA sequence enabling it to replicate in the host cell in question. An example of such a sequence in a mammalian cell is the SV40 origin of replication.

The transfected mammalian cells are cultured in a suitable nutrient medium under conditions permitting the co-expression of FVII and the endoprotease whereupon FVII is recovered from the culture medium. The medium used to culture the mammalian cells may be any medium suitable for growing mammalian cells, such as minimal or complex media containing appropriate supplements. Suitable media are available from commercial suppliers or may be prepared according to published recipes (e.g. in catalogues of the American Type Culture Collection). FVII produced by the cells may then be recovered from the culture medium by conventional procedures including separating the host cells from the medium by centrifugation or filtration, precipitating the proteinaceous components of the supernatant or filtrate by means of a salt, e.g. ammonium sulfate, purification by a variety of chromatographic procedures, e.g. ion exchange chromatography, gelfiltration chromatography, affinity chromatography, or the like, dependent on the type of polypeptide in question.

Separation of the expressed product from the cell culture may be achieved by any method known in the art, including, without limitation, removal of cell culture medium containing the desired product from an adherent cell culture; centrifugation or filtration to remove non-adherent cells; and the like.

Purification of the crude product may be achieved using any method known in the art, including, without limitation, affinity chromatography. In the case of Factor VII or FVII related products one or more of the following methods may be used: an anti-Factor VII antibody column (see, e.g., Wakabayashi et al., *J. Biol. Chem.* 261:11097, 1986; and Thim et al., *Biochem.* 27:7785, 1988); hydrophobic interaction chromatography; ion-exchange chromatography; size exclusion chromatography; electrophoretic procedures (e.g., preparative isoelectric focusing (IEF)), differential solubility (e.g., ammonium sulfate precipitation) or extraction, and the like. See, generally, Scopes, *Protein Purification*, Springer-Verlag, New York, 1982; and *Protein Purification*, J.-C. Janson and Lars Ryden, editors, VCH Publishers, New York, 1989. Following purification, the preparation preferably contains less than about 10% by weight, more preferably less than about 5 wt. % and most preferably less than about 1 wt. %, of non-Factor VII proteins derived from the host cell.

Factor VII and Factor VII-related polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al.,*J. Clin. Invest.* 71:1836 (1983). Alternatively, Factor VII may be activated by passing it through an ion-exchange chromatography column, such as Mono Q® (Pharmacia) or the like. The resulting activated Factor VII may then be formulated and administered as described below.

The Factor VII or FVII related polypeptides produced by the present invention may be used to treat any Factor VII-responsive syndrome, such as, e.g., bleeding disorders, including, without limitation, disorders caused by clotting factor deficiencies (e.g., hemophilia A and B or deficiency of coagulation factors XI or VII); by thrombocytopenia or von Willebrand's disease; by clotting factor inhibitors; or by excessive bleeding from any cause. The preparations may also be administered to patients in association with surgery or other trauma or to patients receiving anticoagulant therapy.

Preparations comprising Factor VII-related polypeptides produced by the method according to the present invention, which have substantially reduced bioactivity relative to wild-type Factor VII, may be used as anticoagulants, such as, e.g., in patients undergoing angioplasty or other surgical procedures that may increase the risk of thrombosis or occlusion of blood vessels as occurs, e.g., in restenosis. Other medical indications for which anticoagulants are prescribed include, without limitation, deep vein thrombosis, pulmonary embolism, stroke, disseminated intravascular coagulation (DIC), fibrin deposition in lungs and kidneys associated with gram-negative endotoxemia, myocardial infarction; Acute Respiratory Distress Syndrome (ARDS), Systemic Inflammatory Response Syndrome (SIRS), Hemolytic Uremic Syndrome (HUS), MOF, and TTP.

Pharmaceutical compositions comprising the Factor VII and Factor VII-related preparations produced according to the present invention are primarily intended for parenteral administration for prophylactic and/or therapeutic treatment. Preferably, the pharmaceutical compositions are administered parenterally, i.e., intravenously, subcutaneously, or intramuscularly. Such compositions may be administered by continuous or pulsatile infusion.

The following examples are intended as non-limiting illustrations of the present invention.

EXAMPLE 1

Cloning and Characterization of SEQ ID NO:1, LRCA2

Subtractive PCR techniques have been used to identify genes which are expressed to high levels in Chinese Hamster (*Cricetulus griseus*) Ovary cells (CHO cells) (Puck, T. T, et al., 1958, "Genetics of somatic mammalian cells, III. Long-term cultivation of euploid cells from human and animal subjects". J. Exp. Med. 108:945–956; Kao F. T. and Puck T. T., 1968, "Genetics of somatic mammalian cells, VII. Induction and isolation of nutritional mutants in Chinese hamster cells". Proc. Natl. Acad. Sci. USA 60:1275–1281). One of the PCR products obtained by this assay, a 2.7 kb fragment was cloned from ECoRV digested CHO DNA (CHO cell line DG44) by use of DNA ollgonucleotides CLC394 AAAACTGGGAACCATTTGTG (SEQ ID NO:9) and CLC56L CTGCAGAAGAGGCGACAG (SEQ ID NO:10) and the PCR-Setect kit (CLONTECH). CLC394L and CLC56L are complementary to the CHO cyclophilin cDNA sequence (GenBank Accession no. X17105).

Subsequent analysis of the flanking sequences led to the isolation of a DNA fragment from the upstream region of the CHO cell cycloohilin gene (Bergsma, D. J. and Sylvester, D., 1990, "A Chinese hamster ovary cyclophilin cDNA sequence". Nucl. Acids Res. 18:200) promoter. This DNA fragment has been identified by computer-analysis (Singh, G. B., Kramer, J. A. and Krawetz, S. A., 1997, "Mathematical model to predict regions of chromatin attachment to the nuclear matrix". Nucl. Acids Res. 25:1419–1425) as a putative S/MAR element, which was named LRCA2, SEQ ID NO:1.

EXAMPLE 2

Cloning and Characterization of SEQ ID NO: 2, B4B1

A recombinant Baby Hamster Kidney cell line expressing a recombinant protein was analyzed for the chromosomal DNA encompassing the integrated plasmid DNA. To this end, chromosomal DNA of the recombinant BHK cell line has been isolated by standard methods. The isolated DNA became subsequently subject of restriction enzyme digest. The restriction enzymes used were characterized as enzymes that did not digest sequences present within the integrated plasmid DNA. Such a restriction digest will give rise to DNA fragments containing all of the integrated plasmid and both up- and downstream flanking chromosomal DNA. Following digest, the generated DNA fragments were subjected to a ligation reaction, aiming at intra-molecular ligation giving raise to circular DNA molecules. These circular fragments were then transfected into bacteria, which subsequently were grown under antibiotic selection pressure. Only bacteria that have been transfected with DNA fragments containing the integrated plasmid DNA, and therefore containing an antibiotic resistance gene, were growing under these circumstances. Analysis of clones resulting from digestion with distinct restriction enzymes revealed that digestion with restriction enzyme HindIII resulted in the largest DNA fragments with about 3,500 base pairs up- and about 3000 base pairs downstream of the integration site. These DNA fragments have been isolated, sequenced and analyzed. The upstream sequence has been identified by computer-analysis (Singh, G. B., Kramer, J. A. and Krawetz, S. A., 1997, "Mathematical model to predict regions of chromatin attachment to the nuclear matrix". Nucl. Acids Res. 25:1419–1425) as constituting a putative S/MAR element, which was named B4B1, SEQ ID NO:2.

EXAMPLE 3

Construction of Reporter Gene Vectors for DNA Transfection

In order to analyze the effect of the S/MAR elements LRCA2 and B4B1 on protein expression yields and expression stability, a series of plasmids has been constructed. These plasmids express a reporter gene Secreted Alkaline Phosphatase (SEAP), from an expression cassette that is or is not flanked by S/MAR elements. These constructs have been cloned as follows:

The plasmid pSEAP2-Hygro-MCS (FIG. 1) was made by cloning of the Hygromycin B resistance gene from pIND (SP1)/Hygro (Invitrogen) as a 1.8 kb AseI (blunt, fill in) fragment in the unique SalI site (blunt, fill in) of pSEAP2-Basic (CLONTECH) and incorporation of a DNA MCS-linker GCTGGGCCCGATATCACCGGTTAAT-TAACTAGTTTAAAC (SEQ ID NO:6) into the unique Eco47III site.

Figure 2:
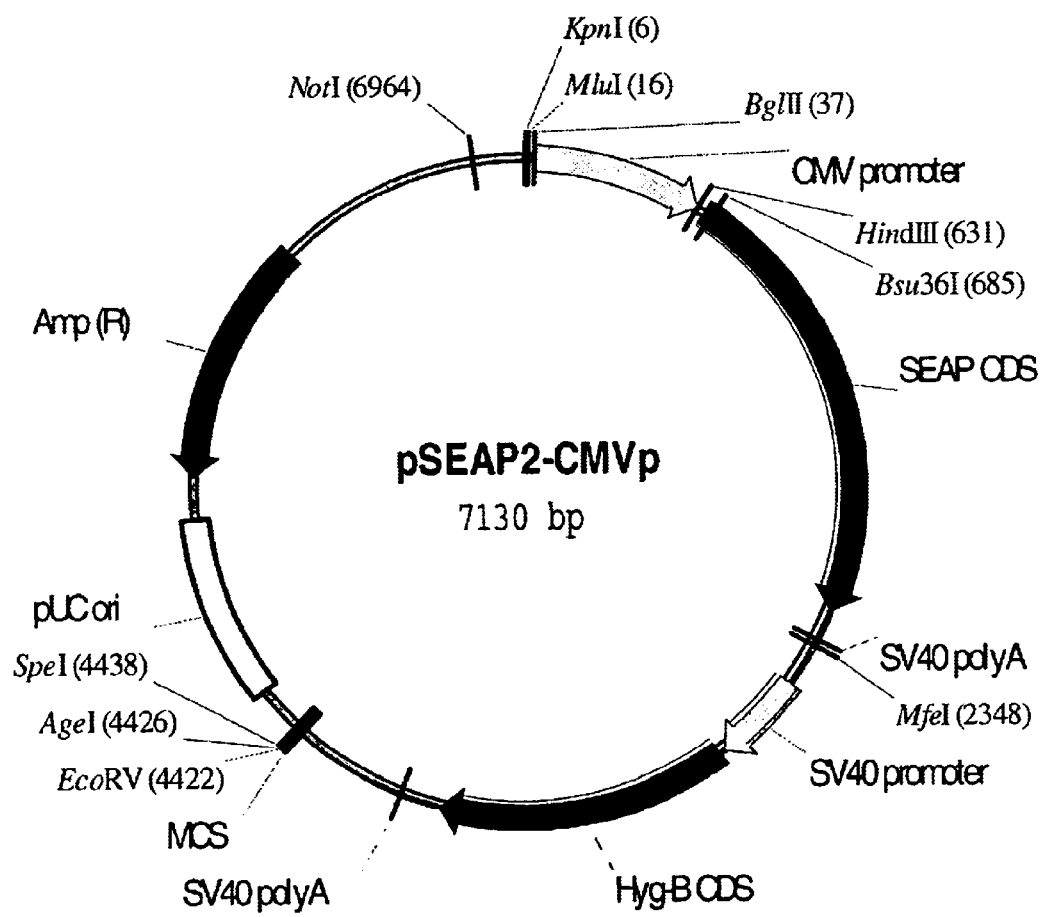
FIG. 2 shows plasmid pSEAP2-CMVp.

To create plasmid pSEAP2-CMVp (FIG. 2) primer JO-252 TATTAAGATCTAGTTATTAATAGTAAT-CAATTAC (SEQ ID NO:7) and primer JO-253 TATATAAGCTTGATCTGACGGTTCACTAAAC (SEQ ID NO:8) were used to generate a 0.6 kb PCR amplified DNA fragment containing the human CMV IE promoter. The fragment was cut with BglII and HindIII before cloning into pSEAP2-Hygro-MCS.

Figure 3:
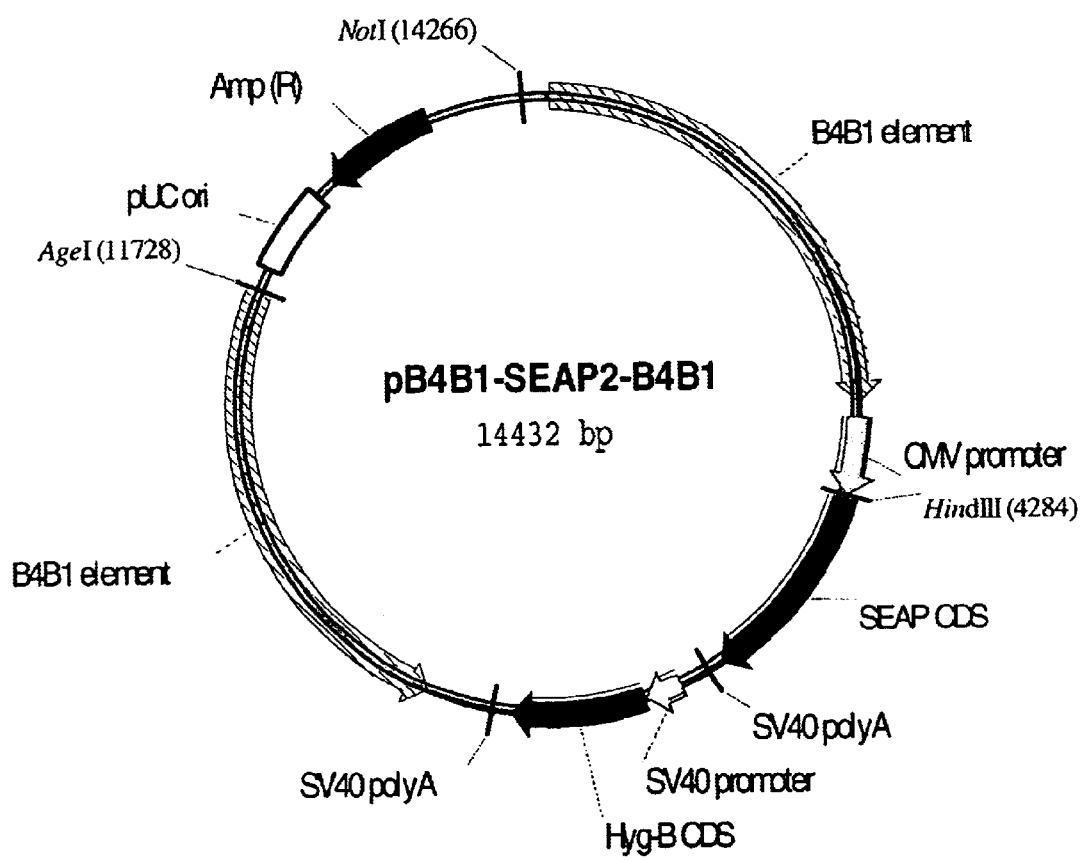
FIG. 3 shows plasmid pB4B1-SEAP2-B4B1.

To create plasmid pB4B1-SEAP2-B4B1 (FIG. 3) pB4B1-SEAP2 and pSEAP2-B4B1 were first made by inserting a 3.6 kb B4B1 BamHI-HindIII (blunt, fill in) fragment at two locations in the pSEAP2-CMVp vector, into the MluI site (blunt, fill in) or into the EcoRV site which generated pB4B1-SEAP2 and pSEAP2-B4B1, respectively. pB4B1-SEAP2 and pSEAP2-B4B1 were cut with HindIII and AgeI and the B4B1 containing DNA fragments from these digests were ligated to generate pB4B1-SEAP2-B4B1.

Figure 4:
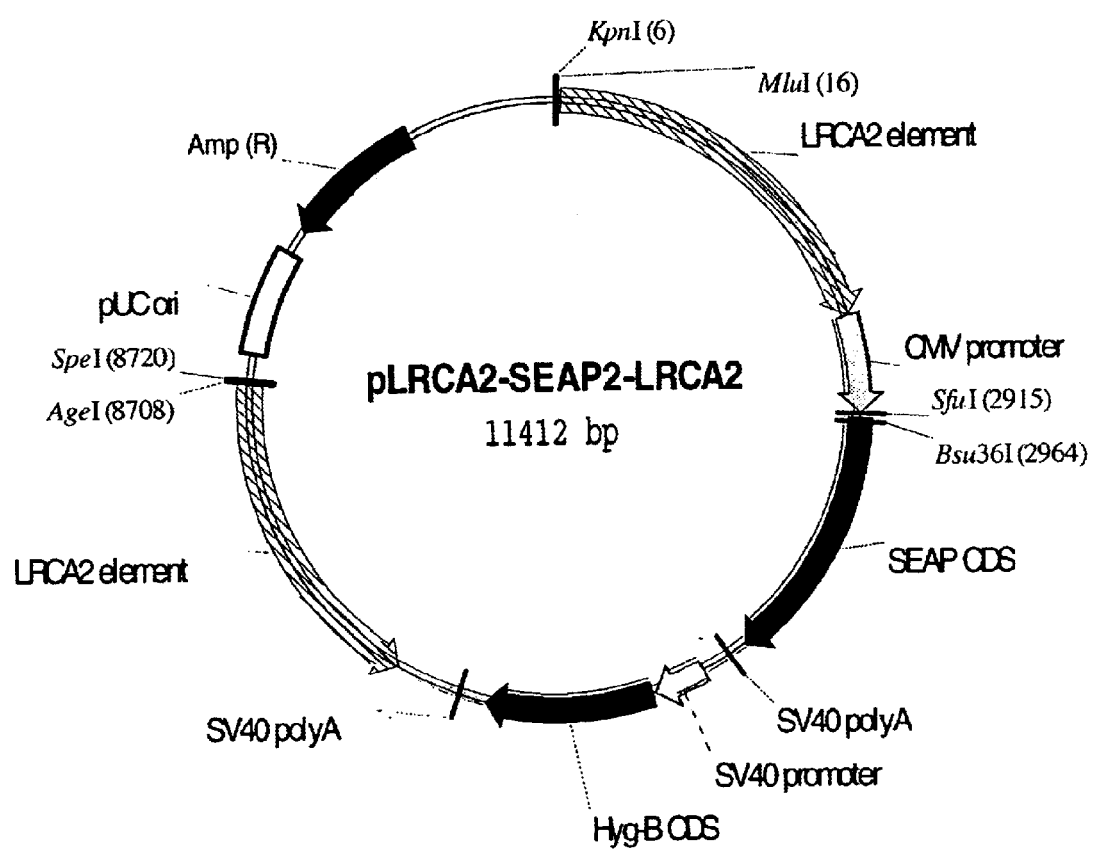
FIG. 4 shows plasmid pLRCA2-SEAP2-LRCA2.

Plasmid pSEAP2-LRCA2 was made by inserting a 2.0 kb LRCA2 HindIII-EcoRI (blunt, fill in) fragment (SEQ ID NO:3) into the EcoRV site of pSEAP2-CMVp. pLRCA2-SEAP2 was made by cloning of a 2.3 kb LRCA2 MluI-BclI fragment (SEQ ID NO:4) in to the MluI-BglII sites of pSEAP2-CMVp. pLRCA2-SEAP2 and pSEAP2-LRCA2 were cut with Bsu36I and AgeI and the LRCA2 containing DNA fragments from these digests were ligated to generate pLRCA2-SEAP2-LRCA2 (FIG. 4).

Figure 5:
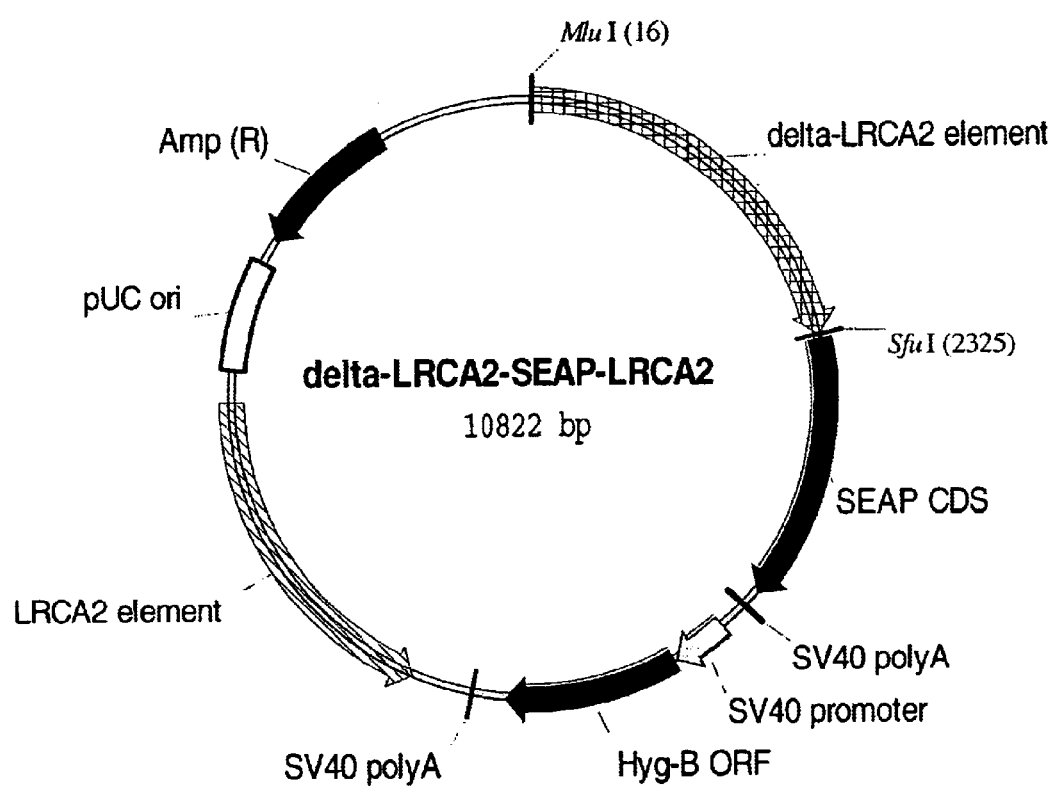
FIG. 5 shows plasmid delta-LRCA2-SEAP2-LRCA2.

The MluI/SfuI LRCA2-CMV fragment in pLRCA2-SEAP2-LRCA2 (FIG. 4) was replaced with a PCR amplified 2.3 kb LRCA2 fragment containing MluI and SfuI restriction sites at the 5' and 3' ends, respectively, generating construct ΔLRCA2-SEAP2-LRCA2 (FIG. 5). The PCR amplified LRCA2 fragment named ΔLRCA2 contains a 12 bp deletion in the large GT-repeat (SEQ ID NO:5).

EXAMPLE 4

Construction of Factor VII cDNA Expression Vectors for DNA Transfection

Figure 6:
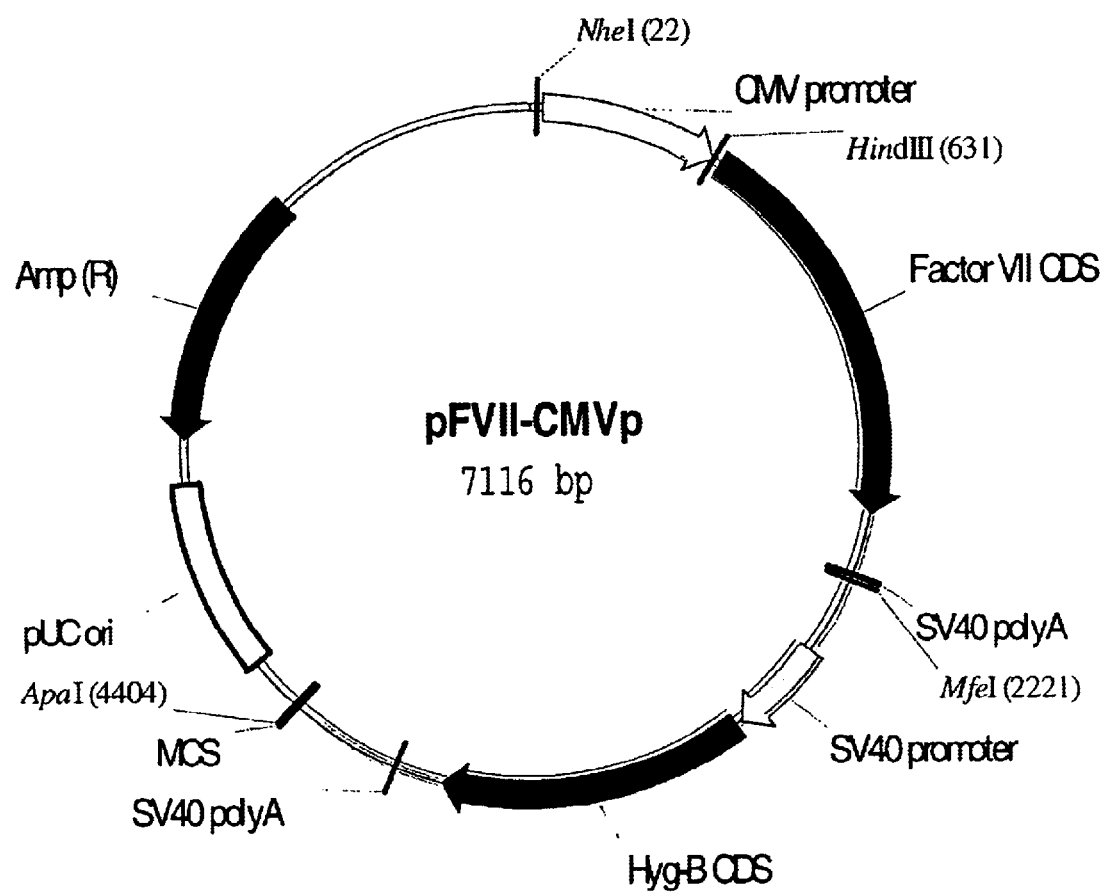
FIG. 6 shows plasmid pFVII-CMVp.

In order to analyze the effect of the S/MAR elements B4B1 and LRCA2 on clone-to-clone variability, expression levels and stability when expressing therapeutic proteins, a series of plasmids has been constructed. The plasmids express a therapeutic protein coagulation factor VII (FVII), from an expression cassette that is or is not flanked by S/MAR elements. The plasmids were made as follows:

To create pFVII-CMVp (FIG. 6), a 1.7 kb HindIII-SalI (blunt, fill in) DNA fragment containing the human Factor VII gene and the SV40 3' UTR/polyA signal was ligated into the HindIII and MfeI (blunt, fill in) sites of vector pSEAP2-CMVp and thereby replacing the SEAP gene.

Figure 7:
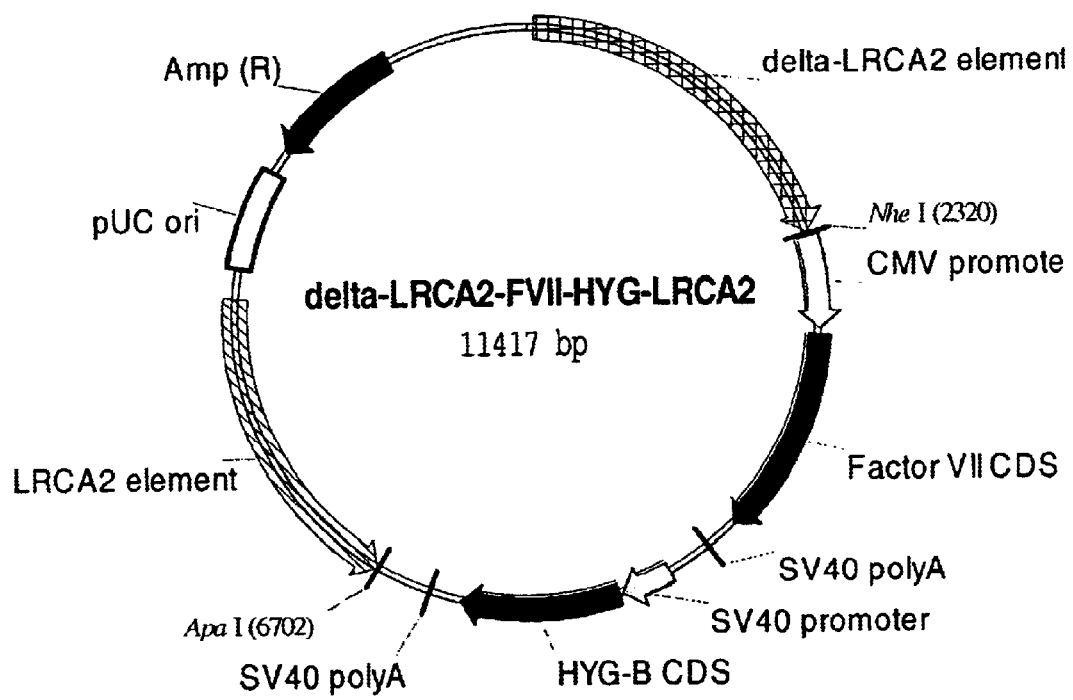
FIG. 7 shows plasmid delta-LRCA2-FVII-HYG-LRCA2.

Factor VII expression vector ΔLRCA2-FVII-HYG-LRCA2 (FIG. 7) was made by cloning of a NheI containing linker sequence at the SfuI site in ΔLRCA2-SEAP2-LRCA2 (FIG. 5). The modified ΔLRCA2-SEAP2-LRCA2 vector was afterwards digested with ApaI and NheI and the 7.0 kb LRCA2 fragment ligated to the 4.4 kb NheI/ApaI fragment from vector pFVII-CMVp (FIG. 6) thus generating vector ΔLRCA2-FVII-HYG-LRCA2 (FIG. 7).

Figure 8:
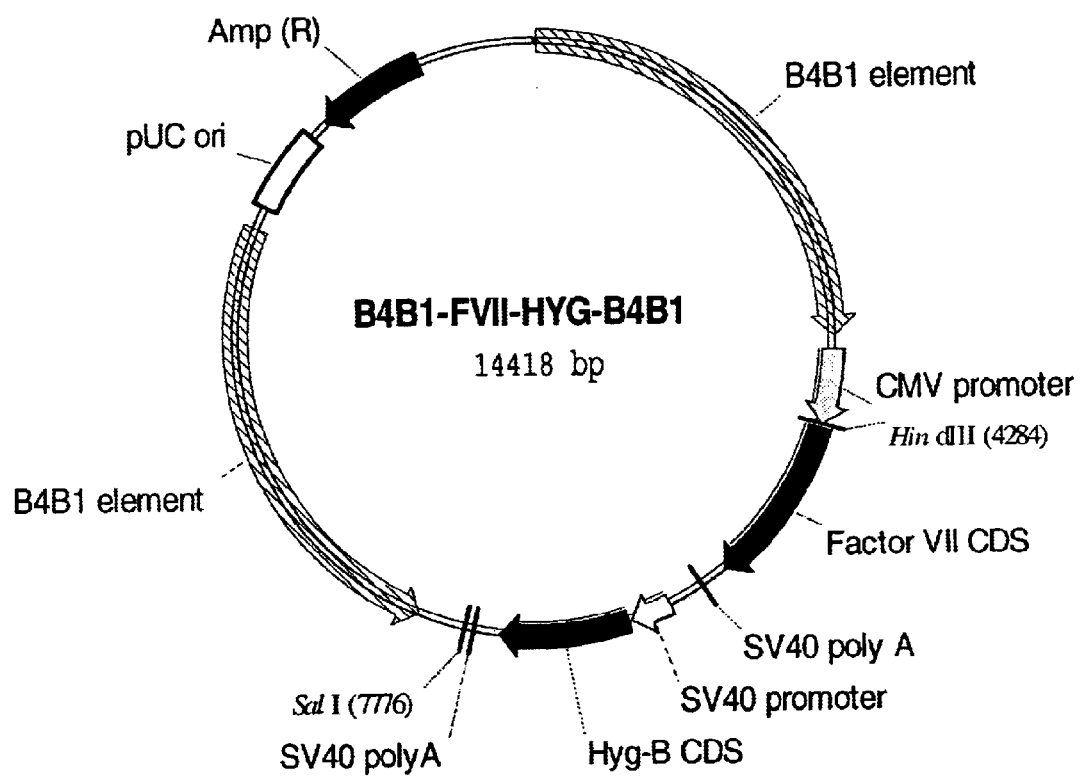
FIG. 8 shows plasmid B4B1-FVII-HYG-B4B1.

The CMV-SEAP-HYG HindIII/SalI fragment from the pB4B1-SEAP2-B4B1 (FIG. 3) construct was replaced with the 3.5 kb HindIII/SalI fragment from the pFVII-CMVp (FIG. 6) construct containing the CMV-FVII-HYG elements, generating the B4B1-FVII-HYG-B4B1 (FIG. 8) construct.

CHO-K1 cells (ATCC CCL-61), cultured in growth medium (Dulbecco's modified Eagle's medium, 10% fetal calf serum, 100 IU penicillin and streptomycin, non-essential amino acids, and 5 mg/l vitamin K1), were transfected using a non-liposomal lipid transfection reagent. FuGENE™ 6 transfection reagent, as per manufacturer's instructions (Roche, Basel, Switzerland). Stable pools of transfectants were obtained by Hygromycin selection as per manufacturer's instructions (Invitrogen, Carlsbad, Calif.). FVII protein yields in the culture medium were determined by standard sandwich ELISA technique (Novo Nordisk), well known to persons skilled in the art.

From the pools of transfectants, a limiting dilution cloning was performed. Briefly, 2 cells pr. well were seeded in 96-well microtiter tissue culture plates in growth medium containing Hygromycin. Following incubation for 13 days medium was replaced, and 24 hr later medium was harvested for FVII ELISA analysis. All samples were compared for FVII expression yields.

Table 1 shows that flanking of the Factor VII expression construct by either B4B1 or LRCA2 leads to decreased variation in expression levels between different founder clones. The median values of the FVII expression levels are also shown where the expression levels obtained from the pCMV-FVII-HYG construct was set to 100% and the others calculated in relation to that. These values show that flanking of the Factor FVII expression construct by either B4B1 or LRCA2 leads to increased FVII expression levels.

|  | pCMV-FVII-HYG | pB4B1-FVII-HYG-B4B1 | pΔLRCA2-FVII-HYG-LRCA2 |
| --- | --- | --- | --- |
| % variation in FVII protein expression | 221 | 141 | 115 |
| Median FVII expression levels, % in relation to pCMV-FVII-HYG expression levels | 100 | 270 | 536 |

EXAMPLE 5

Transfection of Mammalian Cells and SEAP Assay

Chinese Hamster Ovary (CHO) DG44 cells maintained in MEM Alpha medium (Invitrogen, Cat # 22571) supplemented with 5% heat inactivated fetal bovine serum (Invitrogen), 108 mg/L L-proline (Sigma), and penicillin (100 units/ml)/streptomycin (100 μg/ml) (Invitrogen) at 37° C. and 5% $CO_2$ were transfected using a polyamine transfection promoting agent, the GeneJammer® transfection agent (Stratogene), according to the manufactures instructions. Briefly, cells seeded in 6-well cell culture plates were approximately 40–50% confluent on the day of transfection and transfected with 2 μg of linearized plasmid DNA.

To generate hygromycin B resistant cell cultures, transfected cells were, one day post transfection, propagated in MEM Alpha growth medium containing 350 μg/ml hygromycin B (Roche). After 10 to 14 days of selection, wherein the cells were re-fed every $2^{nd}$ or $3^{rd}$ day with selective medium, hygromycin B resistant cells were confluent in the wells. From the day of 100% confluency and forward the cell cultures were split 1:12 to 1:30 every $3^{rd}$ or $4^{th}$ day. On day 29 post transfection cell cultures were split to growth medium without hygromycin. On day 32, 39, and 46 post transfection each cell culture was washed with PBS, trypzined and seeded to approximately 30% confluency in 200 μl growth medium in five wells in a 96-well cell culture plate. After 24 hours of growth at 37° C. and 5% $CO_2$ 100 μl culture supernatant was withdrawn from each micro titer plate well and used for assaying Secreted Alkaline Phosphatase (SEAP) activity. In order to be able to measure specific SEAP production levels each well was assayed for relative cell numbers using Alamar Blue (BioSource International) cell proliferation assay according to the manufactures instructions.

SEAP levels were measured fluorometrically using 4-methylumbelliferyl as substrate: Briefly, the harvested medium was incubated at 65° C. for 15 min to inactivate endogenous alkaline phosphatase and the medium was clarified by centrifugation at 4000×g for 5 min at 4° C. 50 μl of culture supernatant, 2- to 10-fold diluted samples were pippeted into 96-well plates, and development in fluorescence ($Ex_{360\ nm}$ and $Em_{450\ nm}$) was followed as a function of time in a FLUOstar Galaxy (BMG Labtechnologies, Germany) fluorescence microplate reader after addition of 225 μl of 4-methylumbelliferyl phosphate liquid substrate (Sigma).

Figure 9:
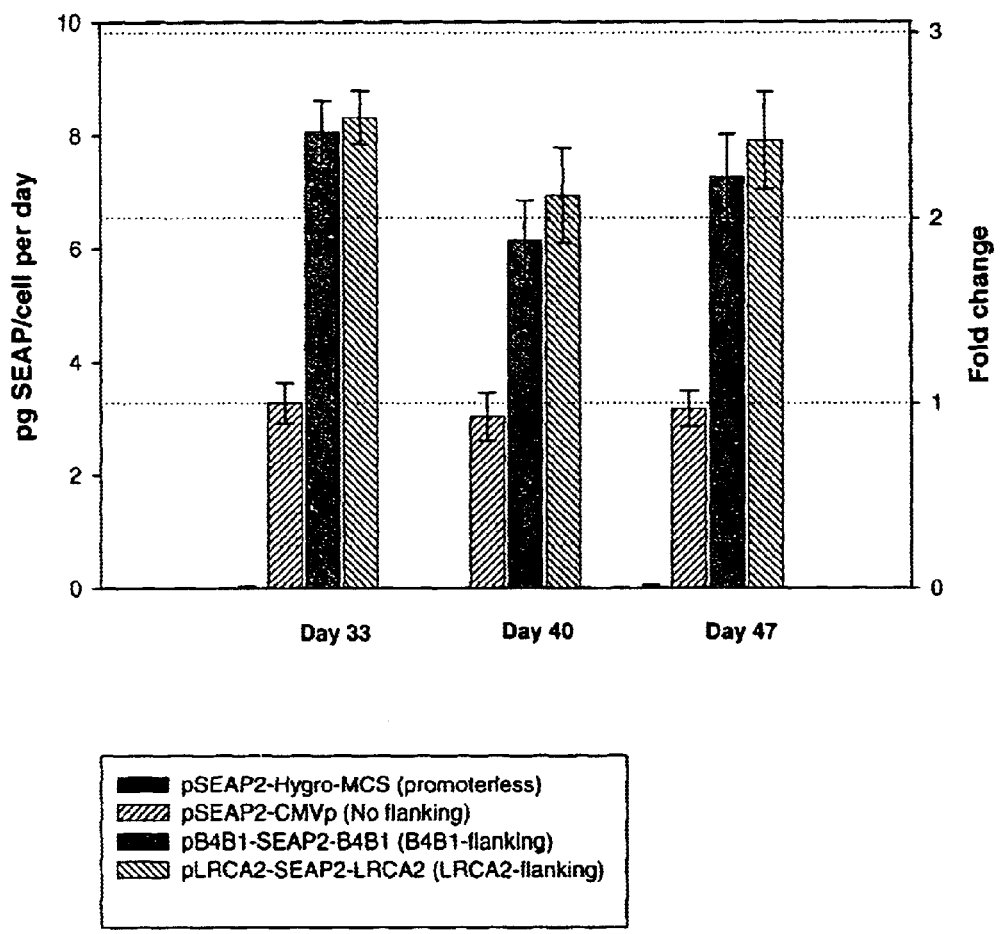
FIG. 9 shows SEAP expression data from transfected CHO cells.

On days 33, 40, and 47 post transfection, stable cell pools transfected with plasmid pSEAP2-Hygro-MCS, pSEAP2-CMVp, pB4B1-SEAP2-B4B1, or pLRCA2-SEAP2-LRCA2 were assayed for SEAP production. In FIG. 9, the results from one such experiment are shown, illustrating that flanking of the SEAP expression construct by either B4B1 or LRCA2 leads to increased expression levels. Additionally, these results illustrate that SEAP expression from such vectors is stable over time.

In another experiment linearized SEAP expression plasmids, pSEAP2-Hygro-MCS, pSEAP2-CMVp, pB4B1-SEAP2-B4B1, or pLRCA2-SEAP2-LRCA2, were electroporated into CHO DG44 cells, according to Baer, et al., 2000 ("Transcriptional properties of genomic transgene integration sites marked by electroporation or retroviral infection". Biochemistry 39:7041–7049). From the pools of transfectants, a limiting dilution cloning was performed. Briefly, two cells per well were seeded in 96-well microtiter tissue culture plates in MEM Alpha growth medium (Invitrogen) containing hygromycin B (Roche, 350 μg/ml). Following incubation for 24 days medium was replaced, and 24 hours later 100 μl medium was harvested for SEAP analysis, as described above. Cell numbers was estimated using Alamar Blue (BioSource International).

Figure 10:
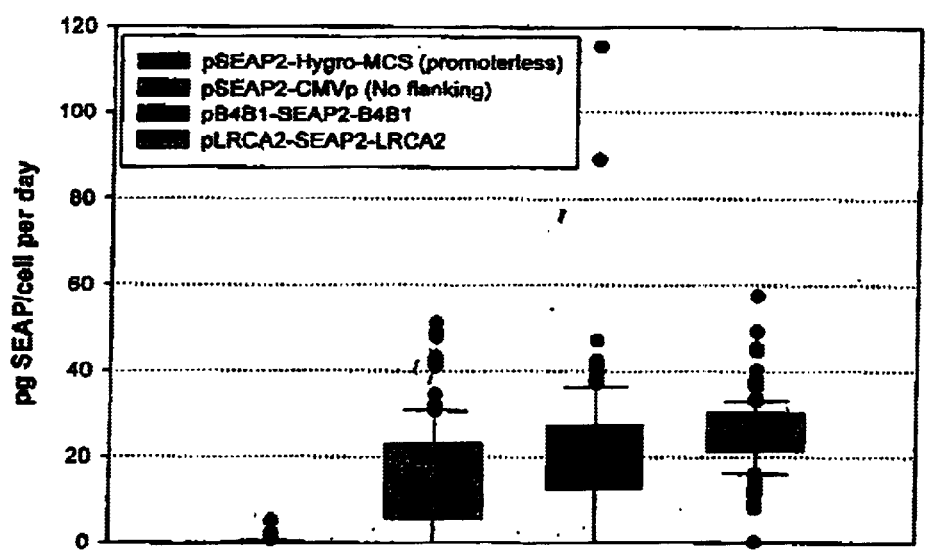
FIG. 10 is a box plot showing statistical values calculated from single cell clone SEAP expressors.

FIG. 10 shows a box plot of the SEAP expression data from DG44 cells transfected with these four different expression plasmids. Upper and lower box boundaries indicate the $25^{th}$ and $75^{th}$ percentiles, respectively. Lines within the boxes mark the median and dashed lines show the mean. Whiskers above and below boxes indicate the $10^{th}$ and $90^{th}$ percentiles. Outlying data points are indicated by filled ovals. Statistics were calculated from 140, 132, 144, and 128 data points, respectively.

EXAMPLE 6

In Vitro Hydrolysis Assay

The following method can be used to assay Factor VIIa bioactivity. The assay is carried out in a microtiter plate (MaxiSorp, Nunc, Denmark). The chromogenic substrate D-Ile-Pro-Arg-p-nitroanilide (S-2288, Chromogenix, Sweden), at a final concentration of 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of a test and a reference Factor VIIa.

EXAMPLE 7

In Vitro Proteolysis Assay

The following method can be used to assay Factor VIIa bioactivity. The assay is carried out in a microtiter plate (MaxiSorp, Nunc, Denmark). Factor VIIa (10 nM) and Factor X (0.8 microM) in a solution of 100 μl 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 μl 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of a test and a reference Factor VIIa.

All patents, patent applications, and literature references referred to herein are hereby incorporated by reference in their entirety.

Many variations of the present invention will suggest themselves to those skilled in the art in light of the above detailed description. Such obvious variations are within the full intended scope of the appended claims.

We claim:

1. A method for producing a protein comprising (a) transfecting a mammalian cell with a nucleic acid molecule comprising (I) a sequence encoding the protein and (II) at least one scaffold/matrix attachment region (S/MAR) element comprising SEQ ID NO: 1, SEQ ID NO: 2, SEQ ID NO: 3, SEQ ID NO: 4, or SEQ ID NO: 5; (b) culturing the transfected cell under conditions suitable for expression of the protein; and (c) isolating the expressed protein.

2. The method of claim 1, wherein the protein is Factor VII or a Factor VII-related polypeptide.

3. The method of claim 2, wherein the nucleic acid molecule comprises two S/MAR elements selected from the group consisting of SEQ ID NO: 1, SEQ ID NO: 2, SEQ ID NO: 3, SEQ ID NO: 4, and SEQ ID NO: 5.

4. The method of claim 3, wherein the two S/MAR elements are identical.

5. The method of claim 4, wherein the identical S/MAR elements comprise SEQ ID NO:1.

6. The method of claim 4, wherein the identical S/MAR elements comprise SEQ ID NO:2.

7. The method of claim 4, wherein the identical S/MAR elements comprise SEQ ID NO:3.

8. The method of claim 4, wherein the identical S/MAR elements comprise SEQ ID NO:4.

9. The method or claim 4, wherein the identical S/MAR elements comprise SEQ ID NO:5.

10. The method of claim 3, wherein the two S/MAR elements comprise SEQ ID NO:1 and SEQ ID NO:2, respectively.

11. The method of claim 3, wherein the two S/MAR elements comprise SEQ ID NO:2 and SEQ ID NO:3, respectively.

12. The method of claim 3, wherein the two S/MAR elements comprise SEQ ID NO:2 and SEQ ID NO:4, respectively.

13. The method of claim 3, wherein the two S/MAR elements comprise SEQ ID NO:2 and SEQ ID NO:5, respectively.

14. The method of claim 2, wherein the at least one S/MAR element is located less than 10 kb from the Factor VII or Factor VII-related polypeptide-encoding sequence.

15. The method of claim 1, wherein the nucleic acid molecule comprises two S/MAR elements selected from the group consisting of SEQ ID NO: 1, SEQ ID NO: 2, SEQ ID NO: 3, SEQ ID NO: 4, and SEQ ID NO: 5.

16. The method of claim 15, wherein the two S/MAR elements are identical.

17. The method of claim 16, wherein the identical S/MAR elements comprise SEQ ID NO:1.

18. The method of claim 16, wherein the identical S/MAR elements comprise SEQ ID NO:2.

19. The method of claim 16, wherein the identical S/MAR elements comprise SEQ ID NO:3.

20. The method of claim 16, wherein the identical S/MAR elements comprise SEQ ID NO:4.

21. The method of claim 16, wherein the identical S/MAR elements comprise SEQ ID NO:5.

22. The method of claim 15, wherein the two S/MAR elements comprise SEQ ID NO:1 and SEQ ID NO:2, respectively.

23. The method of claim 15, wherein the two S/MAR elements comprise SEQ ID NO:2 and SEQ ID NO:3, respectively.

24. The method of claim 15, wherein the two S/MAR elements comprise SEQ ID NO:2 and SEQ ID NO:4, respectively.

25. The method of claim 15, wherein the two S/MAR elements comprise SEQ ID NO:2 and SEQ ID NO:5, respectively.

26. An isolated DNA molecule comprising one or more S/MAR elements that comprise a sequence selected from the group consisting of SEQ ID NO: 1, SEQ ID NO: 2, SEQ ID NO: 3, SEQ ID NO: 4, and SEQ ID NO: 5.

27. The isolated DNA molecule of claim 26, wherein the DNA molecule comprises a sequence encoding a human protein or polypeptide or a functional analogue of a human protein or polypeptide.

28. The isolated DNA molecule of claim 27, wherein the protein or polypeptide-encoding sequence is located less than 10 kb from the one or more S/MAR elements.

29. The isolated DNA molecule of claim 28, wherein the isolated DNA molecule comprises SEQ ID NO:1.

30. The isolated DNA molecule of claim 28, wherein the isolated DNA molecule comprises SEQ ID NO:2.

31. The isolated DNA molecule of claim 28, wherein the isolated DNA molecule comprises SEQ ID NO:3.

32. The isolated DNA molecule of claim 28, wherein the isolated DNA molecule comprises SEQ ID NO:4.

33. The isolated DNA molecule of claim 28, wherein the isolated DNA molecule comprises SEQ ID NO:5.

34. A vector construct comprising a nucleic acid molecule comprising (a) a sequence encoding Factor VII or a Factor VII-related polypeptide operably linked to one or more expression control elements and (b) one or more S/MAR elements selected from the group consisting of SEQ ID NO: 1, SEQ ID NO: 2, SEQ ID NO: 3, SEQ ID NO: 4, and SEQ ID NO: 5.

35. A mammalian cell comprising the vector of claim 34.

36. A vector construct comprising a nucleic acid molecule that comprises (a) a sequence encoding a polypeptide or protein operably linked to one or more expression control elements and (b) at least one S/MAR element comprising a sequence selected from the group consisting of SEQ ID NO: 1, SEQ ID NO: 2, SEQ ID NO: 3, SEQ ID NO: 4, and SEQ ID NO: 5.

37. A mammalian cell comprising the vector of claim 36.

38. An isolated DNA molecule consisting essentially of one or more sequences selected from the group consisting of SEQ ID NO: 1, SEQ ID NO: 2, SEQ ID NO: 3, SEQ ID NO: 4, and SEQ ID NO: 5.

* * * * *

SEQUENCE LISTING

<160> NUMBER OF SEQ ID NOS: 9

<210> SEQ ID NO 1
<211> LENGTH: 2715
<212> TYPE: DNA
<213> ORGANISM: Cricetulus griseus

<400> SEQUENCE: 1

| | | | | | |
|---|---|---|---|---|---|
| ctgcaggaag | aggcgacagg | ggacagcggc | atctgcaaaa | cccataaagt | tattttaagg | 60 |
| tcgttttctt | ctgcttcatc | tgcactggga | tgttcagatg | ttcaggtctt | gctgttgtag | 120 |
| aaccaccagt | ttctggttgt | gccataatgc | tctttatgtt | gtccagtgta | tttttacact | 180 |
| gttgtttacc | catctcttcc | tccaattgta | cagatgaatc | cagtgtttca | ggggtccct | 240 |
| cttcctccaa | ttgatgcaat | tggaggctat | ggctcctttg | atcactcctc | caggagcagg | 300 |
| cagggaagag | cctcaggtga | ttgctcctct | agatgctggc | aggcccaatg | atcatgtggt | 360 |
| cagtcccctg | ggtacaggca | tggccatggc | tccagagatt | gcctcttcca | ggtgcaggca | 420 |
| gggccatggc | tctggtgatc | actcctctag | tgaaaggtgg | gggtctgagg | ctccaatggt | 480 |
| tgttgatgtg | gtagagtatc | tcatacagag | gatagcacta | gatgctgtct | gggacatagg | 540 |
| taagctttcc | agagagactt | cataatatat | tttcttgaag | cctctgctgg | caatacttct | 600 |
| ggggctgctg | cctttctccc | tgtctgattc | ctagggtgag | ggttaccact | gctctctctc | 660 |
| tccctttctc | taaacttct | gggccagggt | agggcacta | ccgcattccc | tctctcttcc | 720 |
| aaacacttct | atttcttgat | ttctatcttg | gctcattttt | aactcagtag | tgagttgttt | 780 |
| ggtttccata | agtttgtaag | ttttctgttg | tttctgttgt | tgttgttgtt | atctagattt | 840 |
| aagctgtggt | ggtcagatag | gacatagagt | attatttcaa | ttgtctttta | tctgtcgaga | 900 |
| cttgctttgt | tttgaaatat | gtattcaatt | tggagagtt | tcatagggtg | ctgacaagaa | 960 |
| ggtacagtct | ttgtgttttg | gtgaaatagt | ctgtaaatat | ctctaggtcc | acttggttta | 1020 |
| tgacatcagt | tagctccagc | atttctctgt | ttcgtttttt | gttgagatga | cctaactgtt | 1080 |
| ggagagaatg | gggtattgaa | gtagcccact | atctgtgtgt | gaggtcaata | tgtgatttta | 1140 |
| gctgtagctg | tgcttgtttt | atgaacttgg | gtgacattgt | gtttggtgca | tagacattaa | 1200 |
| gaattgcaat | gtcctcttgg | tggatttttcc | tttgatgcct | atgtagtatt | cttcccaatc | 1260 |
| tcatctgctt | agttttgggt | ttaagtctat | tagtcagata | ttaaaatgac | tgtatcggct | 1320 |
| tgcttcttag | ggccatttgc | ttagaatatc | ttttccatcc | ttttactcta | aggtgatgtc | 1380 |
| tatccatggt | aggttgtctt | ttttggatgc | agcagtagga | tggatcttgt | tttcatatcc | 1440 |
| attctgttac | ccagtatctt | tttctagaga | aattaagatc | attgagtcat | tgatgttgag | 1500 |
| aattatcaat | gagcagtgtt | tgtggattct | tgttatcttg | cacttgtgaa | gtgtgtgtgt | 1560 |
| gtgtgtgtgt | gtgtgtgtgt | gtgtgtgtgt | gtgtgtgtgt | gtgtgtgtgt | gtgtctgtgt | 1620 |
| ctgtgtcttg | tgtgtctgtg | ttctctcccc | tcttttgatt | tttggcctgg | aattatttat | 1680 |
| tattcatatt | ttcttgaatg | tgggtaacat | ctttagattg | aagttttctc | cctagccttc | 1740 |
| tttaggtctg | catttgaaga | tagatattct | ttacatctga | ttttatctta | gaatgtcttt | 1800 |
| ctttctccaa | ctattgtgac | agaaagtttt | tctaagtgca | gtagtctggc | ctgacatctg | 1860 |
| tagtctcttg | gagtctgtag | cacatctgtg | cagggccttc | ttacattttg | agtttctatt | 1920 |
| ggaaaagtca | ggtgtaattc | taatacatct | gcctttatat | gttaattggt | cttttttccc | 1980 |
| ttgcatcttt | taatattctt | tctttgttct | atacttttag | tgatttgatt | attatgcact | 2040 |

-continued

```
gtggggagtt tcttttccgg tccaatctat ttggtgtttt gtatgcttct tgtaccttga    2100
taggcatctc tttctcaagg ttaggaaatt tttctttttt ggttttcttg aaaatatttt    2160
ccctgctttt gacctgcctt cttccccttc ctctattcct ttggtttttg catagtgtct    2220
ctggcttcct ggatgtttta tgcctggatt attttagact taacattttc tttgaccaag    2280
gtatccattt cttctatctt gtcttcactg cctgagattc tctcttctat ctcttgtatt    2340
ctgtcagtga ggcttgtctc tgaggttcct gttgggttct taattttttc atttccagat    2400
ttccttcagt ttgggttttg tttattaatt ctatttccac tttcaggtcc tgaaatgttt    2460
tactcatttt cctcccagta tttacatttt cataggtttc tttaatggat ttattcattt    2520
cctcttcaag gacctttat gaattcataa aatgtatgtt aaggtccttg ccttgtgctt    2580
cagctatgtt gcattctcag ggcctattgt aatagggttt tagcagggac atattgtcct    2640
ggttgttatt gtctgtgttt ttgctttggc atatagacgg ctgagtttgg gatgattgta    2700
attctaggtg ctgat                                                     2715
```

<210> SEQ ID NO 2
<211> LENGTH: 3572
<212> TYPE: DNA
<213> ORGANISM: Baby hamster kidney cell line

<400> SEQUENCE: 2

```
gtcaggaagg gcggcagtga ggagaggtac ctaccctcgt ccaaggtaag gagcagtagc      60
tgcgctttgc tggagcagcc gtaaagagat accccacgcc caaggtaaga gaaacccaag     120
taagatggta ggtgttgtga gagggcatca gagggcagac atactgaaac catacacgca     180
gaaaactagt caatctaatc acactaggac cacagccttg tctaactcaa tgaaactaag     240
ccatgcccgt ggggcaaccc aagatgggca ggtcatggtg gagagatctg acagaatgtg     300
gtccactgga gaagggaatg caaaccactt cagtattctt gccttgagaa ccccatgaac     360
agtatgaaaa ggcaaaatga taggatactg aaagaggaac tccccaggtc agtaggtgcc     420
ccatatgcta ctggagatca gtggagaaat aactccagaa agaatgaaga gatggagcca     480
aagcaaaaag aatacccagc tgtggatgtg actggtgata taagcaaggt ccgatgctgt     540
aaagagcaat attgcatagg aacctggaat gtcaggtcca tgaatcaagg caaattggaa     600
gtggtcaaac aagagatggc aagagtgaat gtcaacattc taggaatcag cgaactaaaa     660
tggactggaa tgggtgaatt taactcgat gaccattata tctactactg cgggcaggaa     720
tccctcagaa gaaatggagt agccatcatg gtcaacaaaa gagtccgaaa tgcagtactt     780
ggatgcagtc tcaaaaacga cagaatgatc tctgtttgtt tccaaggcaa accattcaat     840
atcacagtaa tccaagtcta tgccccaacc agtaatgctg aagaagctga agttgaacgg     900
tcctatgaag acctacaaga ccttttagaa ctaacaccca aaaagatgt ccttctcatt     960 atagggact ggaatgcaaa agtaggaagc aaagaaacac ctggagtaac aggcaaattt    1020
ggccttggaa tacggaatga agcagggcaa agactaatag agttttgcca agaaaatgca    1080
ctggtcatag caaacaccct cttccaacaa cacaagagaa gactctacac atggacatca    1140
ccagatggtc aacaccgaaa tcagattgat tatattcttt gcagccaaag atggagaagc    1200
tctatacagt cagcaaaaac aagaccagga gcttactgtg gctcagatca tgaactcctt    1260
attgccaaat tcagacttaa attgaagaaa gtagggaaaa ccactagatc actcaggtaa    1320
gacctaaatc caatccctta tgattataca gtggaagtga gaaatagatt taagggccta    1380
```

```
gatctgatag acagagtacc taatgaacta tggacagagg ttcatgacat tgtacaggag   1440
acagggatcg agaccatccc catggaaaag aaatgcaaaa aagcaaaatg gctgtctggg   1500
gaggccttac aaatagctgt gaaaagaaga gaagtgaaaa gcaaaggaaa aaaggaaaga   1560
taaaagcatc tgaatgcaga gttccaaaga acttccagtt gttcaagctg gttttagaaa   1620
agtcagagga accagagacc aaattgccaa catcctctgt atcatggaaa agcaagaga   1680 gttccagaaa aacatctatt tctgctttat tgactatgca aaagcctttg actgtggggg   1740
tcacaataaa ctgtggaaaa ttctgaaagg gatgggaata ccagaccacc tgacctgact   1800
cttgaaaaat ttgtatgcag gtcaggaagc aacagttaga actggacatg gaacaacaga   1860
ctggttccaa gtaggaaaag gagtatgtca aggctgtata ttgtcacccg gcttgtttaa   1920
cttctatgca gagacatcat gagaaacgct gggctgaag aagcacaagc tggaatcaag   1980
attgccggga gaaatagcaa taacctcaga tatgcagatg ataccaccct tatggcagaa   2040
agtgaagagg aactaaaaag cctcttgatg aaggtgaaaa aggagagtga aaagttggc   2100 ttaaagctca acattcagaa aacgaagatc atggcatctg gtcccatcac ttcatgggaa   2160
atagatgggg aaacagtgga aacagtgtca gactttattt ttttgggggc tccaaaatca   2220
ctgcagatgg tgactgcagc catgaaatta aaagacactt actccttgga agaaaagtta   2280
accaacctag atagcatatt gaaaagcaga gacattacct tgccaacaaa gccccatcta   2340
gtcaaggcta tggttttttcc agtggtcatg tatggatgtg agagttggac tgtgaagaaa   2400
gctgagcact gaagaattga tgcttttgaa ctgtggtgtt ggagaagact cttgagagtc   2460
ccttggactg caaggagatc caaccagtcc attctgaagg agatcagccc tgggatttct   2520
ttggaaggaa tgatgctaaa gctgaaactc cagtactttg gccacctgat cagaagagct   2580
gactcactgg aaaagacccct gatgctggga gggattgggg gcaggaggag aagggggacga   2640 cagaggatga gatggctgga tggcatcact gactcgatgg acgtgagtct gggtgaactc   2700
ctggagttgg tgatggacag ggaggcctgt cctgcggcga ttcatggggt cacaaagagt   2760
tggacacgac tgagcaactg aactgaactg aactgtactg aaaccttagt agtttatatt   2820
actcagaaaa tagtaatttc atatgtattc aaaattattt cataatgttg gttaagataa   2880
taagattttc aaattgattt ttatctttga tttttctcta cttatttaat tttgggattt   2940
taactatttc ttcaatgact tgtatttcta atatttactt attctatttt actttaattg   3000
cacttatttt tattgatttt tctaataaaa tccagtcctt gttttttttaa aaagacttta   3060 aaattattaa tttctcttta gtgttttacc agttctttca ggctacttct tttgatttat   3120
ttggtcctat cttttctcaa gttttgaatt ggctacgtaa ctcatttatc tttattttt   3180 gtaaattagc tctttaaatt cattattctt tgataacagc ttcagttcta tggctttaat   3240 aaagttttt ttttttttt tttttaaaga atgtcattct ttgtgaagtt ttgacaatgc   3300
tttgagcaat aatttaggat attttttgaat ggttcatgag tatgcttttg tacttggcat   3360
ttattgaagt ttatgattta tgaattatga tgctttttt tgggcataaa ggtctatggc   3420 atatttttttg tggtctatat tcttaaaatt ataaattggc tttaaaaagt atttgctgct   3480
attaaacatg aattaagtct tatttggact atagtggagt cacaaaagag ttggacatga   3540
cttagcgact aagcaacaac agcagaaagc tt                                 3572
```

<210> SEQ ID NO 3
<211> LENGTH: 2003
<212> TYPE: DNA
<213> ORGANISM: Cricetulus griseus

<400> SEQUENCE: 3

```
agctttccag agagacttca taatatattt tcttgaagcc tctgctggca atacttctgg      60
ggctgctgcc tttctccctg tctgattcct agggtgaggg ttaccactgc tctctctctc     120
cctttctcta acacttctgg gccagggtag gggcactacc gcattccctc tctcttccaa     180
acacttctat ttcttgattt ctatcttggc tcatttttaa ctcagtagtg agttgtttgg     240
tttccataag tttgtaagtt ttctgttgtt tctgttgttg ttgttgttat ctagatttaa     300
gctgtggtgg tcagatagga catagagtat tatttcaatt gtcttttatc tgtcgagact     360
tgctttgttt tgaaatatgt attcaatttt ggagagtttc atagggtgct gacaagaagg     420
tacagtcttt gtgttttggt gaaatagtct gtaaatatct ctaggtccac ttggtttatg     480
acatcagtta gctccagcat ttctctgttt cgttttttgt tgagatgacc taactgttgg     540
agagaatggg gtattgaagt agcccactat ctgtgtgtga ggtcaaatat gtgattttagc     600
tgtagctgtg cttgttttat gaacttgggt gacattgtgt ttggtgcata gacattaaga     660
attgcaatgt cctcttggtg gattttcctt tgatgcctat gtagtattct tcccaatctc     720
atctgcttag ttttgggttt aagtctatta gtcagatatt aaaatgactg tatcggcttg     780
cttcttaggg ccatttgctt agaatatctt ttccatcctt ttactctaag gtgatgtcta     840
tccatggtag gttgtctttt ttggatgcag cagtaggatg gatcttgttt tcatatccat     900
tctgttaccc agtatctttt tctagagaaa ttaagatcat tgagtcattg atgttgagaa     960
ttatcaatga gcagtgtttg tggattcttg ttatcttgca cttgtgaagt gtgtgtgtgt    1020
gtgtgtgtgt gtgtgtgtgt gtgtgtgtgt gtgtgtgtgt gtgtgtgtgt gtctgtgtct    1080
gtgtcttgtg tgtctgtgtt ctctcccctc ttttgatttt tggcctggaa ttatttatta    1140
ttcatatttt cttgaatgtg ggtaacatct ttagattgaa gttttttctcc tagccttctt    1200
taggtctgca tttgaagata gatattcttt acatctgatt ttatcttaga atgtcttcct    1260
ttctccaact attgtgacag aaagttttc taagtgcagt agtctggcct gacatctgta    1320
gtctcttgga gtctgtagca catctgtgca gggccttctt acattttgag tttctattgg    1380
aaaagtcagg tgtaattcta atacatctgc ctttatatgt taattggtct ttttttccctt    1440
gcatcttta atattctttc tttgttctat acttttagtg atttgattat tatgcactgt    1500
ggggagtttc ttttccggtc caatctattt ggtgttttgt atgcttcttg taccttgata    1560
ggcatctctt tctcaaggtt aggaaatttt tcttttttgg ttttcttgaa atatttttcc    1620
ctgctttta cctgccttct tccccttcct ctattccttt ggttttgca tagtgtctct    1680
ggcttcctgg atgttttatg cctggattat tttagactta acattttctt tgaccaaggt    1740
atccatttct tctatcttgt cttcactgcc tgagattctc tcttctatct cttgtattct    1800
gtcagtgagg cttgtctctg aggttcctgt tgggttctta attttttcat ttccagattt    1860
ccttcagttt gggttttgtt tattaattct atttccactt tcaggtcctg aaatgtttta    1920
ctcattttcc tcccagtatt tacatttca taggtttctt taatggattt attcatttcc    1980
tcttcaagga cctttttatga att                                            2003
```

<210> SEQ ID NO 4
<211> LENGTH: 2279
<212> TYPE: DNA
<213> ORGANISM: Cricetulus griseus

<400> SEQUENCE: 4

| | |
|---|---|
| gatcactcct ctagtgaaag gtgggggtct gaggctccaa tggttgttga tgtggtagag | 60 |
| tatctcatac agaggatagc actagatgct gtctgggaca taggtaagct ttccagagag | 120 |
| acttcataat atattttctt gaagcctctg ctggcaatac ttctggggct gctgcctttc | 180 |
| tccctgtctg attcctaggg tgagggttac cactgctctc tctctccctt tctctaacac | 240 |
| ttctgggcca gggtaggggc actaccgcat tccctctctc ttccaaacac ttctatttct | 300 |
| tgatttctat cttggctcat ttttaactca gtagtgagtt gtttggtttc cataagtttg | 360 |
| taagttttct gttgtttctg ttgttgttgt tgttatctag atttaagctg tggtggtcag | 420 |
| ataggacata gagtattatt tcaattgtct tttatctgtc gagacttgct ttgttttgaa | 480 |
| atatgtattc aattttggag agtttcatag ggtgctgaca agaaggtaca gtctttgtgt | 540 |
| tttggtgaaa tagtctgtaa atatctctag gtccacttgg tttatgacat cagttagctc | 600 |
| cagcatttct ctgtttcgtt ttttgttgag atgacctaac tgttggagag aatggggtat | 660 |
| tgaagtagcc cactatctgt gtgtgaggtc aatatgtgat tttagctgta gctgtgcttg | 720 |
| ttttatgaac ttgggtgaca ttgtgtttgg tgcatagaca ttaagaattg caatgtcctc | 780 |
| ttggtggatt ttcctttgat gcctatgtag tattcttccc aatctcatct gcttagtttt | 840 |
| gggtttaagt ctattagtca gatattaaaa tgactgtatc ggcttgcttc ttagggccat | 900 |
| ttgcttagaa tatcttttcc atccttttac tctaaggtga tgtctatcca tggtaggttg | 960 |
| tcttttttgg atgcagcagt aggatggatc ttgtttcat atccattctg ttacccagta | 1020 |
| tcttttcta gagaaattaa gatcattgag tcattgatgt tgagaattat caatgagcag | 1080 |
| tgtttgtgga ttcttgttat cttgcacttg tgaagtgtgt gtgtgtgtgt gtgtgtgtgt | 1140 |
| gtgtgtgtgt gtgtgtgtgt gtgtgtgtgt gtgtgtgtct gtgtctgtgt cttgtgtgtc | 1200 |
| tgtgttctct cccctctttt gattttttggc ctggaattat ttattattca tattttcttg | 1260 |
| aatgtgggta acatctttag attgaagttt tctcctagc cttctttagg tctgcatttg | 1320 |
| aagatagata ttcttttacat ctgattttat cttagaatgt ctttctttct ccaactattg | 1380 |
| tgacagaaag ttttttctaag tgcagtagtc tggcctgaca tctgtagtct cttggagtct | 1440 |
| gtagcacatc tgtgcagggc cttcttacat tttgagtttc tattggaaaa gtcaggtgta | 1500 |
| attctaatac atctgccttt atatgttaat tggtctttttt tcccttgcat cttttaatat | 1560 |
| tcttttctttg ttctatactt ttagtgattt gattattatg cactgtgggg agtttctttt | 1620 |
| ccggtccaat ctatttggtg tttttgtatgc ttcttgtacc ttgataggca tctctttctc | 1680 |
| aaggttagga aattttttctt ttttggtttt cttgaaaata ttttccctgc ttttgacctg | 1740 |
| ccttcttccc cttcctctat tcctttggtt tttgcatagt gtctctggct tcctggatgt | 1800 |
| tttatgcctg gattattta gacttaacat tttctttgac caaggtatcc atttcttcta | 1860 |
| tcttgtcttc actgcctgag attctctctt ctatctcttg tattctgtca gtgaggcttg | 1920 |
| tctctgaggt tcctgttggg ttcttaattt tttcatttcc agatttcctt cagtttgggt | 1980 |
| tttgtttatt aattctatt ccactttcag gtcctgaaat gttttactca ttttcctccc | 2040 |
| agtatttaca ttttcatagg tttctttaat ggatttattc atttcctctt caaggacctt | 2100 |
| ttatgaattc ataaaatgta tgttaaggtc cttgccttgt gcttcagcta tgttgcattc | 2160 |
| tcagggccta ttgtaatagg gttttagcag ggacatattg tcctggttgt tattgtctgt | 2220 |
| gttttttgctt tggcatatag acggctgagt ttgggatgat tgtaattcta ggtgctgat | 2279 |

<210> SEQ ID NO 5
<211> LENGTH: 2267

<212> TYPE: DNA
<213> ORGANISM: Cricetulus griseus

<400> SEQUENCE: 5

| | | | | | |
|---|---|---|---|---|---|
| gatcactcct | ctagtgaaag | gtggggtct | gaggctccaa | tggttgttga | tgtggtagag | 60 |
| tatctcatac | agaggatagc | actagatgct | gtctgggaca | taggtaagct | ttccagagag | 120 |
| acttcataat | atattttctt | gaagcctctg | ctggcaatac | ttctggggct | gctgcctttc | 180 |
| tccctgtctg | attcctaggg | tgagggttac | cactgctctc | tctctccctt | tctctaacac | 240 |
| ttctgggcca | gggtagggc | actaccgcat | tccctctctc | ttccaaacac | ttctatttct | 300 |
| tgatttctat | cttggctcat | ttttaactca | gtagtgagtt | gtttggtttc | cataagtttg | 360 |
| taagttttct | gttgtttctg | ttgttgttgt | tgttatctag | atttaagctg | tggtggtcag | 420 |
| ataggacata | gagtattatt | tcaattgtct | tttatctgtc | gagacttgct | ttgttttgaa | 480 |
| atatgtattc | aattttggag | agtttcatag | ggtgctgaca | agaaggtaca | gtctttgtgt | 540 |
| tttggtgaaa | tagtctgtaa | atatctctag | gtccacttgg | tttatgacat | cagttagctc | 600 |
| cagcattttct | ctgtttcgtt | ttttgttgag | atgacctaac | tgttggagag | aatgggtat | 660 |
| tgaagtagcc | cactatctgt | gtgtgaggtc | aatatgtgat | tttagctgta | gctgtgcttg | 720 |
| ttttatgaac | ttgggtgaca | ttgtgtttgg | tgcatagaca | ttaagaattg | caatgtcctc | 780 |
| ttggtggatt | ttcctttgat | gcctatgtag | tattcttccc | aatctcatct | gcttagtttt | 840 |
| gggtttaagt | ctattagtca | gatattaaaa | tgactgtatc | ggcttgcttc | ttagggccat | 900 |
| ttgcttagaa | tatcttttcc | atccttttac | tctaaggtga | tgtctatcca | tggtaggttg | 960 |
| tctttttttgg | atgcagcagt | aggatggatc | ttgttttcat | atccattctg | ttacccagta | 1020 |
| tcttttctta | gagaaattaa | gatcattgag | tcattgatgt | tgagaattat | caatgagcag | 1080 |
| tgtttgtgga | ttcttgttat | cttgcacttg | tgaagtgtgt | gtgtgtgtgt | gtgtgtgtgt | 1140 |
| gtgtgtgtgt | gtgtgtgtgt | gtgtgtctgt | gtctgtgtct | tgtgtgtctg | tgttctctcc | 1200 |
| cctcttttga | tttttggcct | ggaattattt | attattcata | ttttcttgaa | tgtgggtaac | 1260 |
| atctttagat | tgaagttttt | ctcctagcct | tcttttaggtc | tgcatttgaa | gatagatatt | 1320 |
| ctttacatct | gattttatct | tagaatgtct | ttctttctcc | aactattgtg | acagaaagtt | 1380 |
| tttctaagtg | cagtagtctg | gcctgacatc | tgtagtctct | tggagtctgt | agcacatctg | 1440 |
| tgcagggcct | tcttacattt | tgagtttcta | ttggaaaagt | caggtgtaat | tctaatacat | 1500 |
| ctgcctttat | atgttaattg | gtcttttttc | ccttgcatct | tttaatattc | tttcttgtt | 1560 |
| ctatactttt | agtgatttga | ttattatgca | ctgtggggag | tttcttttcc | ggtccaatct | 1620 |
| atttggtgtt | ttgtatgctt | cttgtacctt | gataggcatc | tctttctcaa | ggttaggaaa | 1680 |
| ttttctttt | ttggttttct | tgaaaatatt | ttccctgctt | ttgacctgcc | ttcttcccct | 1740 |
| tcctctattc | ctttggtttt | tgcatagtgt | ctctggcttc | ctggatgttt | tatgcctgga | 1800 |
| ttatttaga | cttaacattt | tctttgacca | aggtatccat | ttcttctatc | ttgtcttcac | 1860 |
| tgcctgagat | tctctcttct | atctcttgta | ttctgtcagt | gaggcttgtc | tctgaggttc | 1920 |
| ctgttgggtt | cttaattttt | tcatttccag | atttccttca | gtttgggttt | tgtttattaa | 1980 |
| ttctatttcc | actttcaggt | cctgaaatgt | tttactcatt | ttcctcccag | tatttacatt | 2040 |
| ttcataggtt | tcttttaatgg | atttattcat | ttcctcttca | aggacctttt | atgaattcat | 2100 |
| aaaatgtatg | ttaaggtcct | tgccttgtgc | ttcagctatg | ttgcattctc | agggcctatt | 2160 |
| gtaatagggt | tttagcaggg | acatattgtc | ctggttgtta | ttgtctgtgt | ttttgctttg | 2220 |

```
gcatatagac ggctgagttt gggatgattg taattctagg tgctgat                    2267

<210> SEQ ID NO 6
<211> LENGTH: 39
<212> TYPE: DNA
<213> ORGANISM: Synthetic

<400> SEQUENCE: 6
gctgggcccg atatcaccgg ttaattaact agtttaaac                             39

<210> SEQ ID NO 7
<211> LENGTH: 34
<212> TYPE: DNA
<213> ORGANISM: Synthetic

<400> SEQUENCE: 7
tattaagatc tagttattaa tagtaatcaa ttac                                  34

<210> SEQ ID NO 8
<211> LENGTH: 34
<212> TYPE: DNA
<213> ORGANISM: Synthetic

<400> SEQUENCE: 8
tattaagatc tagttattaa tagtaatcaa ttac                                  34

<210> SEQ ID NO 9
<211> LENGTH: 20
<212> TYPE: DNA
<213> ORGANISM: Synthetic

<400> SEQUENCE: 9
aaaactggga accatttgtg                                                  20
```